(12) United States Patent
Smith et al.

(10) Patent No.: US 10,695,011 B2
(45) Date of Patent: Jun. 30, 2020

(54) X-RAY COLLIMATOR FOR IMAGING SYSTEM

(71) Applicant: General Electric Company, Schenectady, NY (US)

(72) Inventors: Brandon Smith, Waukesha, WI (US); Gregory Gabrysiak, Waukesha, WI (US); Timothy Behlmer, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 16/058,641

(22) Filed: Aug. 8, 2018

(65) Prior Publication Data

US 2020/0051708 A1 Feb. 13, 2020

(51) Int. Cl.
*A61B 6/06* (2006.01)
*A61B 6/03* (2006.01)
*G21K 1/04* (2006.01)

(52) U.S. Cl.
CPC .............. *A61B 6/06* (2013.01); *A61B 6/035* (2013.01); *G21K 1/04* (2013.01)

(58) Field of Classification Search
CPC ........... A61B 6/03; A61B 6/032; A61B 6/035; A61B 6/06; A61B 6/4035; A61B 6/4078; G21K 1/02; G21K 1/04
See application file for complete search history.

(56) References Cited

U.S. PATENT DOCUMENTS

| | | | | |
|---|---|---|---|---|
| 4,181,858 A | * | 1/1980 | Moore | A61B 6/032 378/157 |
| 5,237,599 A | * | 8/1993 | Gunji | A61B 6/022 378/145 |
| 6,501,828 B1 | * | 12/2002 | Popescu | A61B 6/06 378/145 |
| 7,170,975 B2 | | 1/2007 | Distler et al. | |
| 7,254,216 B2 | * | 8/2007 | Thandiackal | A61B 6/032 378/157 |
| 7,317,786 B2 | | 1/2008 | Distler et al. | |
| 7,522,695 B2 | * | 4/2009 | Nishide | A61B 6/032 250/370.09 |
| 8,699,668 B2 | | 4/2014 | Demianovich, II | |
| 8,976,934 B2 | | 3/2015 | Demianovich | |

(Continued)

*Primary Examiner* — Thomas R Artman
(74) *Attorney, Agent, or Firm* — The Small Patent Law Group LLC; Dean D. Small

(57) ABSTRACT

A collimator includes a panel and one or more blades. The panel defines an exit port, and the one or more blades are held between the panel and an X-ray source to cover at least a portion of the exit port. Each of the one or more blades has a primary blocking member and a secondary blocking member with material densities sufficient to block X-ray radiation. The primary blocking member shapes an X-ray beam emitted from the X-ray source. The secondary blocking member is secured in a fixed position relative to the primary blocking member between the primary blocking member and the panel to block scatter radiation from the X-ray beam from emanating through the exit port. The primary blocking member has a substantially non-planar surface facing toward the X-ray source. The secondary blocking member has a substantially planar surface facing toward the X-ray source.

20 Claims, 6 Drawing Sheets

(56) References Cited

U.S. PATENT DOCUMENTS

| | | | |
|---|---|---|---|
| 9,138,196 B2 | 9/2015 | Zhu | |
| 9,173,619 B2 * | 11/2015 | Oota | A61B 6/032 |
| 9,237,875 B2 * | 1/2016 | Pan | A61B 6/06 |
| 9,312,038 B2 * | 4/2016 | Takagaki | A61B 6/06 |
| 9,724,053 B2 * | 8/2017 | Oota | A61B 6/032 |
| 9,808,209 B2 | 11/2017 | Wang et al. | |
| 2014/0079179 A1 * | 3/2014 | Takagaki | A61B 6/06 |
| | | | 378/4 |
| 2014/0146949 A1 * | 5/2014 | Pan | A61B 6/06 |
| | | | 378/152 |
| 2019/0099136 A1 | 4/2019 | Ogata et al. | |
| 2020/0051708 A1 * | 2/2020 | Smith | A61B 6/06 |

* cited by examiner

X-RAY COLLIMATOR FOR IMAGING SYSTEM

FIELD

The subject matter disclosed herein relates generally to imaging systems, and more particularly, to X-ray collimators for shaping X-ray imaging beams.

BACKGROUND

Non-invasive imaging broadly encompasses techniques for generating images of the internal structures or regions of a subject, such as a person or object. One such imaging technique is known as X-ray computed tomography (CT). CT imaging systems measure the attenuation of X-ray beams that pass through the subject from numerous angles (often referred to as projection data). Based upon these measurements, a computer can process and reconstruct images of the portions of the subject responsible for the radiation attenuation.

Collimators are used to size and shape a beam of X-rays from a source (such as an X-ray tube) so that only the X-ray radiation traveling in desired directions can pass through to the subject being imaged. The collimator may be made from a material that substantially blocks X-rays. The collimator defines an aperture that allows the portion of the incoming X-ray beam moving in the desired direction to pass through the collimator to the subject and then to a detector of the imaging system which measures the attenuation of the X-ray beam through the subject.

The X-ray beam through the aperture of the collimator is projected onto the detector. For good image reconstruction, it is desirable that all or a given portion of a detector be uniformly covered by X-rays from the source. Some known CT imaging systems use detectors that are generally rectangular and curved with respect to a plane that is transverse to the X-ray beam. Use of a substantially planar collimator results in undesirable beam projection coverage of the detector because the beam projection through the flat aperture is distorted (e.g., a different shape) relative to the shape of the curved detector. This distortion reduces the efficiency of the imaging system because only the portions of the beam projection that overlap the curved detector are utilized for image reconstruction. The areas of the beam projection outside of the detector unnecessarily expose the subject to excessive radiation that is not utilized for image reconstruction.

To size and shape the X-ray beam to better match the curved detector than the planar collimators, some known CT imaging systems have collimators with curved surfaces that define the aperture. Although the curved collimators can size and shape the imaging beam to match the detector, the curved collimators generally are not able to block scatter X-ray radiation from escape from the collimator towards the subject. This scatter X-ray radiation is partially-attenuated X-rays that are reflected and/or refracted by various internal features of the collimator. The escaping scatter radiation may be absorbed by the subject, thereby unnecessarily increasing the dosage to the subject, without being received by the detector and used for image reconstruction.

Thus, presently known collimators result in undesired overdoses of X-ray exposure.

BRIEF DESCRIPTION

In one or more embodiments, a collimator is provided that includes a panel and one or more blades. The panel defines an exit port through which an X-ray beam from an X-ray source emanates towards a detector. The one or more blades are held between the panel and the X-ray source and cover at least a portion of the exit port. Each of the one or more blades has a primary blocking member and a secondary blocking member with material densities sufficient to block X-ray radiation. The primary blocking member is configured to shape the X-ray beam that is emanated through the exit port. The secondary blocking member is secured in a fixed position relative to the primary blocking member between the primary blocking member and the panel to block scatter radiation from the X-ray beam from emanating through the exit port. The primary blocking member has a substantially non-planar surface facing toward the X-ray source, and the secondary blocking member has a substantially planar surface facing toward the X-ray source.

In one or more embodiments, a collimator is provided that includes a panel and one or more blades. The panel defines an exit port configured to allow an X-ray beam from an X-ray source to emanate therethrough towards a detector. The one or more blades are held between the panel and the X-ray source and cover at least a portion of the exit port. Each of the one or more blades includes a base, a primary blocking member, and a secondary blocking member. The base has a first side facing the X-ray source. The primary blocking member is mounted to the first side of the base and has a material density sufficient to block X-ray radiation. The primary blocking member has a substantially non-planar surface facing toward the X-ray source that is configured to shape the X-ray beam that is emanated through the exit port. The secondary blocking member is mounted to the base in a fixed position relative to the primary blocking member and is disposed between the primary blocking member and the panel. The secondary blocking member has a material density sufficient to block X-ray radiation. The secondary blocking member includes a substantially planar surface facing toward the X-ray source that is configured to block scatter X-ray radiation from emanating through the exit port. The substantially non-planar surface of the primary blocking member has a concave profile relative to the secondary blocking member such that a middle of the concave profile is closer to the secondary blocking member than each of a first end and a second end of the concave profile.

In one or more embodiments, a collimator is provided that includes a first blade and a second blade spaced apart from each other to define an aperture therebetween. The first and second blades are configured to receive an X-ray beam from an X-ray source and to shape the X-ray beam via the aperture. At least one of the first and second blades is moveable relative to other blade to adjust a size of the aperture. Each of the first and second blades includes a base, a primary blocking member, and a secondary blocking member. The base has a first side facing the X-ray source and a second side opposite the first side. The primary blocking member is mounted to the first side of the base. The secondary blocking member is mounted to the second side of the base and is secured in a fixed position relative to the primary blocking member. The primary blocking member and the secondary blocking member have material densities sufficient to block X-ray radiation. The primary blocking member has a substantially non-planar surface facing toward the X-ray source that shapes the X-ray beam. The secondary blocking member has a substantially planar surface facing toward the X-ray source that blocks scatter X-ray radiation. The aperture has a depth that includes a first passage and a second passage. The first passage is defined between respective inner edges of the primary blocking members of the first and second blades. The second passage is defined between respective inner edges of the secondary blocking members of the first and second blades.

DETAILED DESCRIPTION OF THE INVENTION

Figure 1:
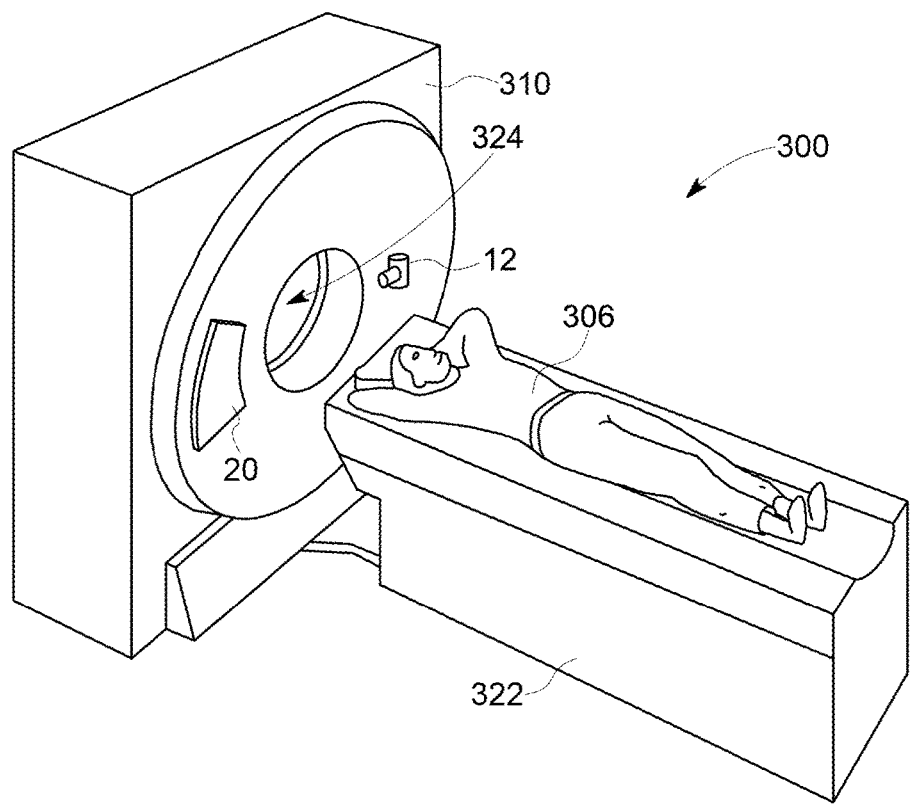
FIG. 1 illustrates an imaging system that is formed in accordance with various embodiments.

The foregoing summary, as well as the following detailed description of various embodiments, will be better understood when read in conjunction with the appended drawings. To the extent that the figures illustrate diagrams of the functional blocks of the various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

The embodiments described herein provide a collimator that defines an aperture for shaping an X-ray beam that traverses from the collimator to a subject and a detector for imaging the subject. The collimator includes two X-ray radiation blocking members on each blade. A primary blocking member receives the incoming X-ray beam and blocks some of the X-rays to shape an outgoing imaging beam such that the projection of the imaging beam matches the size and shape of the detector. A secondary blocking member of each blade is disposed along an opposite side of the primary blocking member relative to the X-ray source, and blocks scatter X-ray radiation from emanating beyond the collimator to the subject. A technical effect of the various embodiments described herein is a reduction in the amount of lower energy scatter X-ray radiation received by the subject that is being imaged, which is radiation that is not utilized for image reconstruction. Another technical effect is substantial alignment between the projected X-ray beam from the collimator and the detector, which reduces or eliminates over-beaming (e.g., projecting X-ray radiation outside of the detector). A combined effect of both aspects is that the collimator described in the embodiments herein may offer improved radiation dose efficiency relative to known collimators. The radiation dose efficiency represents the amount of radiation utilized for image reconstruction (e.g., received by the detector) relative or compared with the amount of radiation applied to the subject or the total amount of generated radiation.

FIG. 1 illustrates an imaging system 300 that is formed in accordance with various embodiments. The imaging system 300 is a CT imaging system. The imaging system 300 includes an X-ray source 12 that emits X-ray radiation in the form of an X-ray beam towards a subject 306 being imaged. The image system 300 includes a detector 20 positioned on an opposite side of the subject 306 from the X-ray source 12. In operation, the X-rays pass through the subject 306 and impinge the detector 20. The detector 20 generates X-ray attenuation measurements, or projection data, based on the radiation that impinges the detector 20, and the projection data is processed to reconstruct an internal image of the subject 306.

The imaging system 300 in FIG. 1 also has a gantry 310 that holds the X-ray source 12 and the detector 20. The imaging system 300 includes a motorized table 322 that receives the subject 306. The motorized table 322 is controlled to move at least a portion of the subject 306 into the gantry 310 through a gantry opening 324. The X-ray source 12 and the detector 20 are separated from each other by the gantry opening 324. The X-ray source 12 and the detector 20 are held on a portion of the gantry 310 that rotates about the subject 306 in the gantry opening 324 during operation to obtain projection data from various angles.

Figure 2:
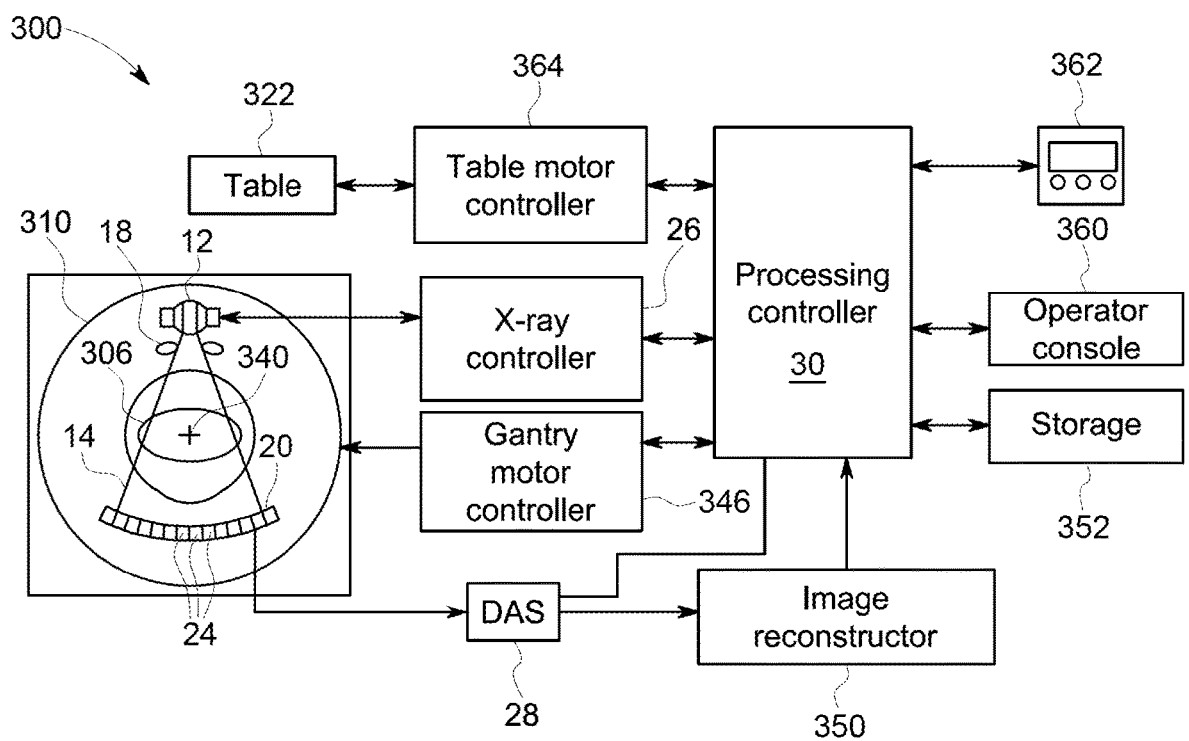
FIG. 2 is a block schematic diagram of a portion of the imaging system shown in FIG. 1.

FIG. 2 is a block schematic diagram of a portion of the imaging system 300 shown in FIG. 1. The imaging system 300 also includes a collimator 18 that is disposed between the X-ray source 12 and the subject 306. Thus, the collimator 18 is a pre-patient collimator. The collimator 18 may also be referred to as a beam limiter because the collimator 18 defines an aperture that limits the angular range of the X-ray beam 14 emitted by the source 12 in one or more dimensions. The collimator 18 shapes the X-ray beam 14 to a generally cone-shaped or fan-shaped beam that impinges upon the subject 306. The collimator 18 may be adjustable to accommodate different scan modes, such as to provide a narrow fan-shaped beam in a helical scan mode and a wider cone-shaped beam in an axial scan mode.

Although not shown in FIG. 2, the imaging system 300 may also include a filter disposed between the X-ray source 12 and the collimator 18. The filter may be a bowtie filter suitable for varying the intensity of the beam 14 to compensate for different thicknesses of the subject 306 as seen from different angular positions of the X-ray source 12.

During a scan, the gantry 310 and the components mounted thereon rotate about a center of rotation 340. The X-ray source 12 and the detector 20 rotate relative to the subject 306 such that the angle at which the X-ray beam 14 intersects the subject 306 changes over time. The X-ray source 12 may be an X-ray tube or the like that emits X-rays from a focal spot. Optionally, the X-ray source 12 may be configured to adjust the location of the focal spot.

The detector 20 in the illustrated embodiment is curved along a direction generally transverse to the X-ray beam 14. The detector 20 includes a plurality of detector elements 24 arranged in multiple rows to form an array of detector elements 24 (although only one row of elements 24 is shown in FIG. 2). The detector elements 24 receive the X-ray beam 14 that is attenuated after traveling through the subject 306. The detector elements 24 measure X-ray attenuation to generate projection data, which is electrical signals that represent properties of the incident X-rays, such as intensity. The projection data is collected and processed to reconstruct images of one or more features or structures within the subject 306.

The imaging system 300 includes a processing controller 30 that is communicatively connected to the detector 20 via a wired or wireless communication path. The processing controller 30 receives the projection data from the detector 20 and processes the projection data to reconstruct an image of the subject 306. The reconstructed image may correspond to a two-dimensional slice taken through the subject 306. The processing controller 30 includes or represents one or more processors and/or other logic-based device(s) that perform operations based on instructions stored on a tangible and non-transitory computer readable storage medium or memory. The processing controller 30 may additionally or alternatively include one or more hard-wired devices that perform operations based on hard-wired logic of the devices. The processing controller 30 may represent the hardware that operates based on software or hardwired instructions, the software that directs hardware to perform the operations, or a combination thereof.

In the illustrated embodiment, the processing controller 30 is operatively connected to a table motor controller 364, an X-ray controller 26, a gantry motor controller 346, a data acquisition system (DAS) 28, an operator console 360, a storage device 352, an image reconstructor 350, and a display unit 362. The table motor controller 364 is operated by the processing controller 30 to control the motorized table 322 to position the subject 306 in the gantry opening 324 (shown in FIG. 1) of the gantry 310. The X-ray controller 26 is configured to provide power and timing signals to the X-ray source 12. The gantry motor controller 346 controls the rotational speed and position of the gantry 310. The DAS 28 receives the projection data collected by readout electronics of the detector 20. The DAS 28 may receive sampled analog signals from the detector 20 and convert the data to digital signals for subsequent processing by the processing controller 30. The image reconstructor 350 receives the sampled and digitized data from the DAS 28 and performs high-speed image reconstruction. The reconstructed images may be input to the processing controller 30 that stores the images in the storage device 352. The processing controller 30 may receive commands and scanning parameters from an operator via an input device, such as the operator console 360 (which may have a keyboard). An associated display unit 362 may display the reconstructed images and other data from the processing controller 30 for observation by the operator.

Although a CT imaging system 300 is illustrated and described, the collimator 18 according to the embodiments described herein may be utilized with other types of CT imaging systems (e.g., specialized CT imaging systems for specific body parts, etc.) and/or non-CT imaging systems.

Figures 3, 4:
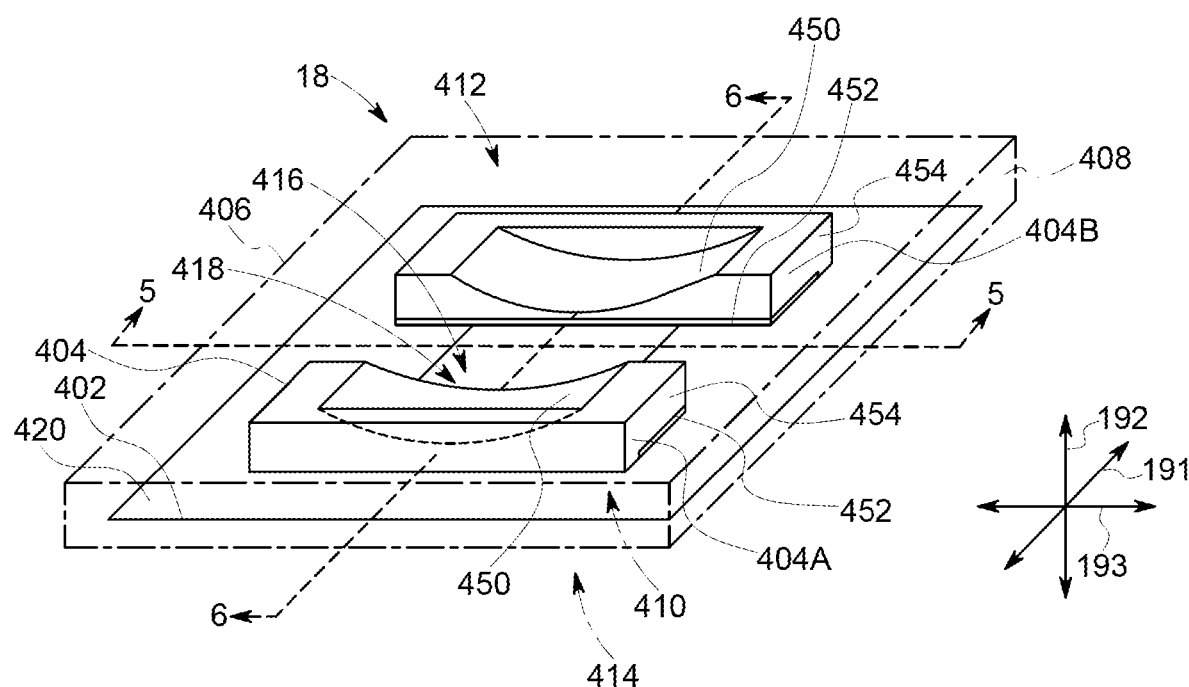
FIG. 3 is a perspective view of a collimator of the imaging system according to an embodiment.
FIG. 4 is a plan view of a source-facing side of the collimator according to an embodiment.

FIG. 3 is a perspective view of the collimator 18 of the imaging system 300 according to an embodiment. The collimator 18 includes a panel 402, one or more blades 404, and a housing 406. The housing 406 includes multiple walls 408 that define and partially enclose a cavity 410. The one or more blades 404 and the panel 402 may be disposed within the cavity 410 of the housing 406. The housing 406 is shown in phantom in FIG. 3 to view the one or more blades 404 and the panel 402 that may otherwise be obstructed by the walls 408 of the housing 406. In the illustrated embodiment, the collimator 18 has two blades 404A, 404B. The two blades 404A, 404B are spaced apart from one another.

The collimator 18 is oriented with respect to a lateral axis 191, a height axis 192, and a longitudinal axis 193. The axes 191-193 are mutually perpendicular. Although the height axis 192 appears to extend in a vertical direction parallel to the direction of gravity in FIG. 3, it is understood that the axes 191-193 are not required to have any particular orientation with respect to the direction of gravity. With reference to FIG. 2, the height axis 192 represents a beam axis because the X-ray beam 14 is emitted from the X-ray source 12 above the collimator 18 and generally propagates along the height axis 192 through the collimator 18 to the subject 306 and the detector 20 located on the other side of (e.g., below) the collimator 18.

The collimator 18 has a first side 412 and an opposite second side 414. The first side 412 faces the X-ray source 12 (shown in FIG. 2) and can be referred to herein as the source-facing side 412. The second side 414 faces the detector 20 (FIG. 2) and can be referred to as the detector-facing side 414. In the illustrated orientation, the source-facing side 412 is a top side, and the detector-facing side 414 is a bottom side. As used herein, relative or spatial terms such as "front," "back," "rear," "upper," "lower," "top," and "bottom," are only used to identify and distinguish the referenced elements in the illustrated orientations and do not necessarily require particular positions or orientations relative to gravity and/or the surrounding environment of the collimator 18. For example, it is recognized that the gantry 310 holding the collimator 18 rotates during operation, such that the orientation of the collimator 18 may be inverted from the illustrated orientation during periods of time. But, the orientation of the collimator 18 relative to the X-ray source 12 and the detector 20 is constant, such that the source-facing side 412 always faces towards the X-ray source 12 and the detector-facing side 414 always faces towards the detector 20.

The collimator 18 defines an aperture 416 through which an imaging portion of the X-ray beam 14 emanates towards the detector 20. For example, the shape and size of the aperture 416 limits or defines the shape and size of the projection of the fan-shaped or cone-shaped beam 14 onto the detector 20. The collimator 18 is composed of one or more appropriate materials of sufficient material density and thickness to block the passage of X-rays through the solid portions of the collimator 18 surrounding the aperture 416. The aperture 416 is an opening extending through the thickness of the collimator 18 between the top and bottom sides 412, 414 to allow passage of X-rays. Therefore, the rays that are received at the aperture 416 pass through the collimator 18 towards the subject 306 and the detector 20, and the rays that impinge upon the collimator 18 outside of the aperture 416 are blocked (or at least significantly attenuated).

The aperture 416 in the illustrated embodiment is partially defined by the panel 402 and by each of the blades 404A, 404B. The panel 402 is planar and defines an exit port 418 therethrough. The blades 404A, 404B are both disposed along a top, source-facing side 420 of the panel 402 and cover respective portions of the exit port 418. The blades 404A, 404B cover the portions of the exit port 418 by extending or projecting beyond edges of the panel 402 that define the exit port 418.

FIG. 4 is a plan view of the source-facing side 412 of the collimator 18 according to an embodiment. The housing 406 is not shown in FIG. 4. In the illustrated embodiment, a lateral width 424 (e.g., parallel to the lateral axis 191) of the exit port 418 is defined between two lateral edges 426 of the panel 402. A longitudinal length 428 (e.g., parallel to the longitudinal axis 193) of the exit port 418 is defined between two longitudinal edges 430 of the panel 402. The exit port 418 is rectangular in the illustrated embodiment, and the longitudinal edges 430 are shorter than the lateral edges 426, but the exit port 418 may have other shapes in other embodiments. The two blades 404A, 404B are elongated parallel to the lateral edges 426. The first blade 404A projects beyond one of the lateral edges 426 and covers a first area 432 of the exit port 418. The second blade 404B projects beyond the other lateral edge 426 and covers a second area 434 of the exit port 418 across from the first area 432.

In the illustrated embodiment, the aperture 416 of the collimator 18 is longitudinally constrained between the longitudinal edges 430 of the panel 402 defining the exit port 418, and laterally constrained between the two blades 404A, 404B. For example, the longitudinal length of the aperture 416 coincides with (e.g., matches) the length 428 of the exit port 418. The lateral width 436 of the aperture 416 is defined between respective inner ends 438 of the two blades 404A, 404B. The lateral width 436 of the aperture 416 is less than the lateral width 424 of the exit port 418.

One or both blades 404A, 404B may be movable relative to the panel 402 to adjust the portion(s) of the exit port 418 covered by the blades 404A, 404B for resizing and/or reshaping the aperture 416. The size and/or shape of the aperture 416 may be modified for shaping the X-ray beam 14 that emanates through the aperture 416, such as to better align the X-ray projection with the detector 20. For example, one or both blades 404A, 404B may be manually repositionable or may be translated via an automated actuator device. In the illustrated embodiment, the collimator 18 includes two rails 442 that engage ends of the blades 404A, 404B. The rails 442 are elongated parallel to the lateral axis 191. An actuator 444, such as a motor and associated circuitry, is coupled to one of the rails 442. The actuator 444 is configured to translate one or both blades 404A, 404B parallel to the lateral axis 191 to selectively adjust the lateral width 436 of the aperture 416 by controlling the relative spacing between the two blades 404A, 404B. In an alternative embodiment, only one of the blades 404A, 404B (e.g., the first blade 404A) is movable by the actuator 444 relative to the panel 402, and the other blade (e.g., the second blade 404B) is fixed and immovable relative to the panel 402. In another alternative embodiment, the collimator 18 only has one blade 404 (e.g., the first blade 404A), and the lateral width 436 of the aperture 416 is defined between the inner end 438 of the first blade 404A and the lateral edge 426 of the panel 402. The single blade 404 may be movable relative to the panel 402 to adjust the size of the aperture 416 for shaping the X-ray beam.

Referring now back to FIG. 3, the first and second blades 404A, 404B may be replica or copies of one another, such that the same equipment (e.g., molds) and tools may be used to produce both blades 404A, 404B. The second blade 404B is arranged on the collimator 18 to mirror the first blade 404A across the aperture 416. Because the blades 404A, 404B may be copies of each other, the following description of one blade 404 may be applicable to both blades 404A, 404B. The blade 404 includes a primary blocking member 450 and a secondary blocking member 452. The secondary blocking member 452 is disposed between the primary blocking member 450 and the panel 402. Both the primary and secondary blocking members 450, 452 have material densities and thicknesses sufficient to block X-ray radiation. The blade 404 also has a base 454 that holds the primary and secondary blocking members 450, 452 in fixed positions relative to one another. Therefore, as the blade 404 moves relative to the panel 402 to adjust the aperture 416, both the primary and second blocking members 450, 452 move with the blade 404 as an integral unit. The blades 404A, 404B are shown and described in more detail herein.

Figure 5:
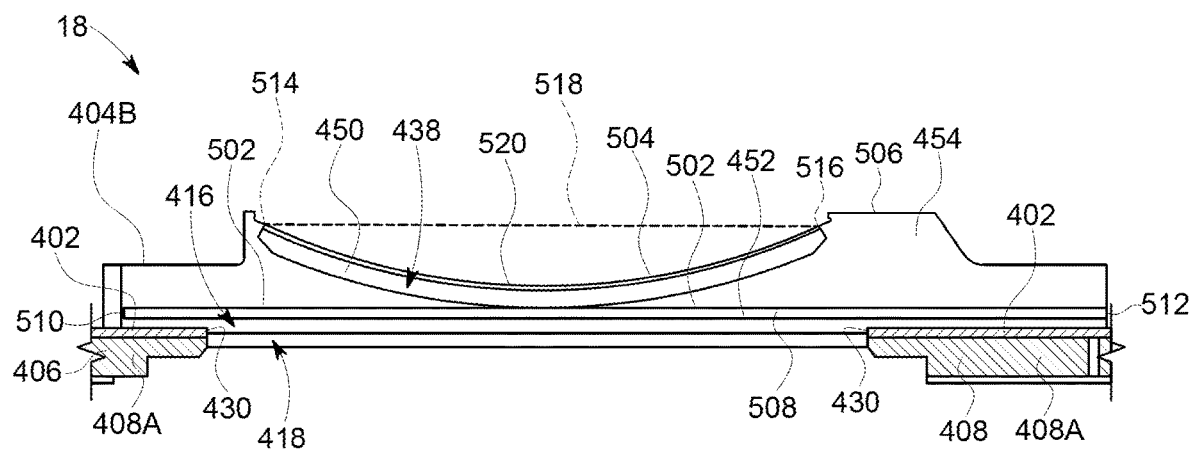
FIG. 5 is a cross-sectional view of the collimator showing a blade according to an embodiment.

FIG. 5 is a cross-sectional view of the collimator 18 showing the second blade 404B according to an embodiment. The cross-section is taken along the line 5-5 in FIG. 3, which extends parallel to the longitudinal axis 193 and traverses across the aperture 416 between the two blades 404A, 404B. Only the panel 402 and a wall 408 of the housing 406 (e.g., a bottom wall 408A) are sectioned in the illustrated embodiment, because the blade 404B is disposed behind the line 5-5. The side view of the blade 404B faces towards the inner end 438 of the blade 404B that defines a portion of the aperture 416, and shows the various components of the blade 404B including primary blocking member 450, the secondary blocking member 452, and the base 454. FIG. 5 also shows the longitudinal edges 430 of the panel 402 that define the longitudinal length 428 (shown in FIG. 4) of the exit port 418 and the aperture 416.

The base 454 holds the primary and secondary blocking members 450, 452 in fixed designated positions relative to each other. The base 454 also mounts the blocking members 450, 452 to the collimator 18. In an embodiment, the base 454 has a material density that is less than the respective material densities of the primary and secondary blocking members 450, 452. For example, the base 454 may not be able to substantially attenuate X-rays that directly impinge on the base 454. The base 454 may include a metal, such as aluminum, that is relatively light-weight to limit the weight of the collimator 18. A low-weight collimator 18 is beneficial for reducing inertial forces as the gantry 310 (shown in FIG. 1) rotates. The base 454 has a first side 506 and a second side 508 that is opposite the first side 506. The first side 506 faces towards the X-ray source 12, and the second side 508 faces towards the detector 20. The first side 506 is a top side in the illustrated orientation, and the second side 508 is a bottom side.

As shown in FIG. 5, the panel 402 is planar and is disposed along the bottom wall 408A of the housing 406. For example, the panel 402 may be secured to the bottom wall 408A or held against the bottom wall 408A. The panel 402 may include lead, tungsten (e.g., raw tungsten), tungsten polymer, or the like, that allows the panel 402 to block or at least substantially attenuate X-ray radiation that impinges upon the panel 402.

The secondary blocking member 452 is disposed between the primary blocking member 450 and the panel 402. The secondary blocking member 452 is mounted to the second (e.g., bottom) side 508 in the illustrated embodiment, but may be held at an intermediate position between the two sides 506, 508 of the base 454 in an alternative embodiment. The secondary blocking member 452 has a substantially planar surface 502 that faces towards the primary blocking member 450 and the X-ray source 12 (shown in FIG. 2). The substantially planar surface 502 is a top surface of the plate in the illustrated orientation and extends along the length of the surface 502 between a first end 510 and an opposite, second end 512 of the secondary blocking member 452. The substantially planar surface 502 may be fully linear and planar or almost fully linear and planar such that any segments of the surface 502 that have different angles or curves are within a designated threshold of one another, such as within 1% or 2%, to give the appearance and overall effect of a linear and planar surface 502. The composition of the secondary blocking member 452 may include lead, tungsten (e.g., raw tungsten), tungsten polymer, or the like, that allows the secondary blocking member 452 to block X-ray radiation, or more specifically scatter radiation. Optionally, the secondary blocking member 452 may be a plate. Although the secondary blocking member 452 is spaced apart from the panel 402 in FIG. 5, the blocking member 452 may engage the panel 402 in an alternative embodiment.

The primary blocking member 450 is mounted to the first (e.g., top) side 506 of the base 454. The primary blocking member 450 has a substantially non-planar surface 504 that faces away from the secondary blocking member 452 and towards the X-ray source 12 (shown in FIG. 2). The substantially non-planar surface 504 is a top surface of the primary blocking member 450 in the illustrated orientation. The surface 504 extends a length between a first end 514 and an opposite second end 516 of the primary blocking member 450. The substantially non-planar surface 504 is non-linear and non-planar along the length between the two ends 514, 516. For example, the substantially non-planar surface 504 curves or slopes away from a phantom line 518 extending between the two ends 514, 516. The substantially non-planar surface 504 may have one or more segments that are angled and/or curved or spaced apart greater than a designated threshold from the line 518, such that it is apparent that the surface 504 is not linear and not planar. The composition of the primary blocking member 450 may include lead, tungsten (e.g., raw tungsten), tungsten polymer, or the like, that allows the primary blocking member 450 to block X-ray radiation that impinges on the substantially non-planar surface 504.

In an embodiment, the shape of the substantially non-planar surface 504 of the primary blocking member 450 may correspond to the shape of the detector 20 (shown in FIG. 2). For example, the surface 504 in FIG. 5 has a curved profile. The profile extends from the first end 514 of the primary blocking member 452 to the second end 516. The profile is concave relative to the secondary blocking member 452 because the first and second ends 514, 516 are spaced apart a greater distance from the secondary blocking member 452 than a middle 520 of the concave curved profile, which is located closer to the secondary blocking member 452. The middle 520 is approximately equidistant between the two ends 514, 516. In the illustrated embodiment, the concave profile of the surface 504 is a continuous curve that extends from the first end 514 to the second end 516. For example, the surface 504 is defined by a single curved segment. The concave curved profile of the surface 504 of the primary blocking member 452 may have a geometry (e.g., arc shape) that corresponds to or matches the geometry of the curved detector 20. As a result, the primary blocking member 452 may shape the X-ray beam that is emitted from the collimator 18 to project onto substantially the entire imaging surface of the detector 20 with very little, if any, over-beaming beyond the imaging surface of the detector. The substantially non-planar surface 504 may have other shapes in other embodiments, as described herein.

Figure 6:
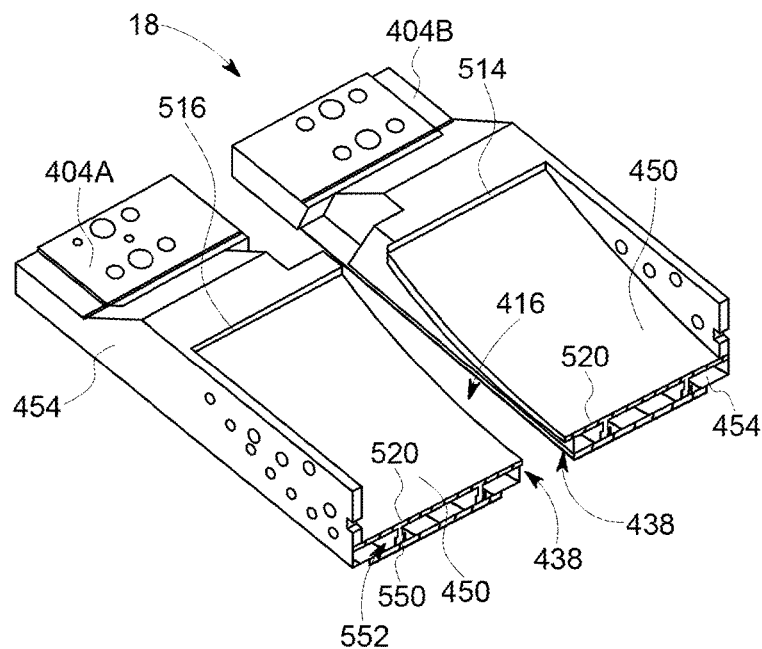
FIG. 6 is a perspective cross-sectional view of the collimator showing first and second blades according to an embodiment.

FIG. 6 is a perspective cross-sectional view of the collimator 18 showing the first and second blades 404A, 404B according to an embodiment. The cross-section is taken along the line 6-6 in FIG. 3, which extends parallel to the lateral axis 191 and traverses across the aperture 416 and both of the blades 404A, 404B. For example, the section line 6-6 may intersect the middle 520 of the curved profile of each of the primary blocking members 450. The inner ends 438 of the two blades 404A, 404B define the lateral width of the aperture 416. Due to the curved profile of the primary blocking members 450, the ends 514, 516 are vertically raised above the middle 520. The variation in height may affect the scatter of X-ray radiation. For example, X-rays that impinge upon the blades 404A, 404B at or proximate to the ends 514, 516 may scatter at different angles relative to X-rays that impinge closer to the middle 520. Some of the scatter radiation from the tall regions near the ends 514, 516 may be directed towards the low regions at the middle 520. As described herein, the secondary blocking member 452 (shown in FIG. 7) is configured to block at least some of the scatter radiation to reduce the amount of scatter radiation emitted through the collimator 18 to the subject 306 (shown in FIG. 2).

In an embodiment the base 454 of each of the blades 404A, 404B is or includes aluminum, and the primary blocking member 450 is or includes tungsten polymer. The primary blocking member 450 may be mounted to the base 454 via molding, such as injection molding. For example, the primary blocking member 450 may be anchored by posts 550 that extend into holes 552 in the base 454. In an alternative embodiment, the primary blocking member 450 may be formed separately from the base 454 and subsequently mounted to the base 454 via fasteners, adhesives, an interference fit, or the like.

Figure 7:
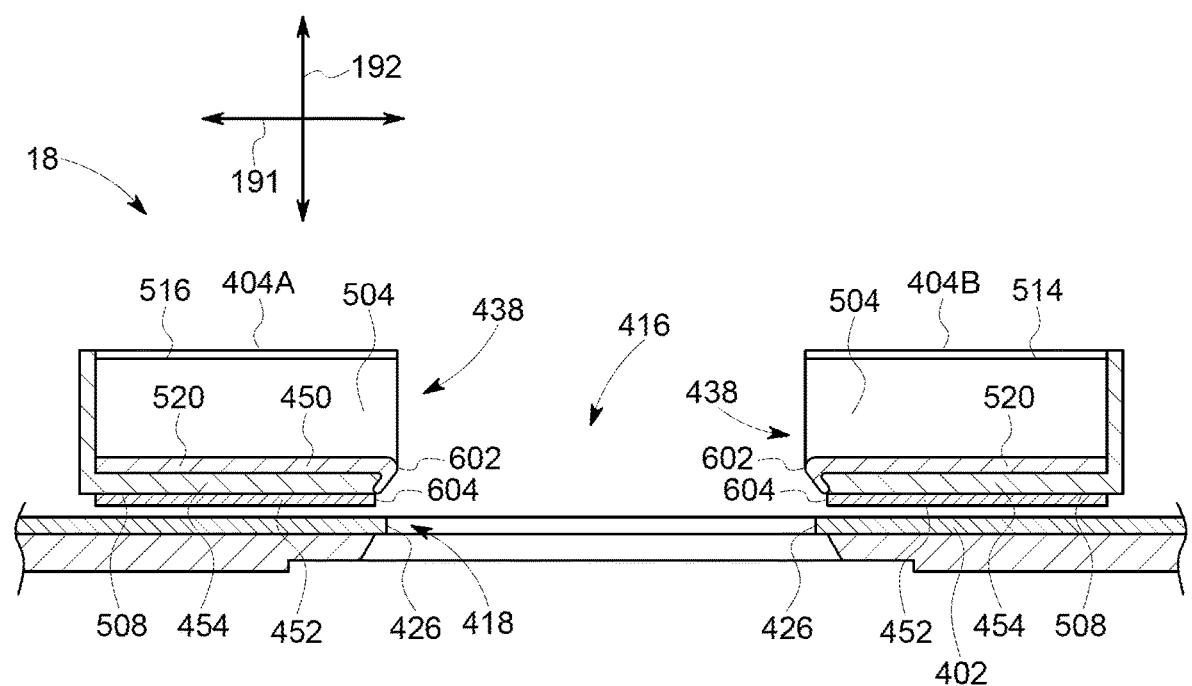
FIG. 7 is a side cross-sectional view of the collimator along the same cross-section line as shown in FIG. 6.

FIG. 7 is a side cross-sectional view of the collimator 18 along the same section line 6-6 as FIG. 6. The lateral width of the aperture 416 is defined between the inner ends 438 of the blades 404A, 404B. In the illustrated embodiment, the lateral width of the aperture 416 has a depth (e.g., along the height axis 192) that includes a first passage and a second passage. The first passage is defined between respective inner edges 602 of the primary blocking members 450 of the blades 404A, 404B. The second passage is defined between respective inner edges 604 of the secondary blocking members 452. The exit port 418 may represent a third passage of the aperture 416. The exit port 418 which is defined between the lateral edges 426 of the panel 402. The second passage is disposed between the first and the exit port 418. The exit port 418 has a fixed width. In an embodiment, the lateral widths of the first and second passages are adjustable by moving one or both of the blades 404A, 404B parallel to the lateral axis 191. The primary and second blocking members 450, 452 of each of the blades 404A, 404B are secured in fixed positions relative to each other, so any adjustment of the blades 404A, 404B equally affects the widths of both the first and second passages.

The primary blocking members 450 of the blades 404A, 404B are configured to receive portions (e.g., X-rays) of an incoming X-ray beam from the X-ray source 12 (shown in FIG. 2) that directly impinge upon the substantially non-planar surfaces 504. The surfaces 504 absorb or otherwise block and attenuate the X-rays that impinge thereon. The secondary blocking members 452 are configured to block scatter radiation from the X-ray beam from emanating through the exit port 418. Each of the secondary blocking members 452 may cover at least a majority of the second side 508 of the base 454, as shown in FIGS. 5 and 7, or may only cover a minority of the base 454 that is proximate to the aperture 416.

Figure 8:
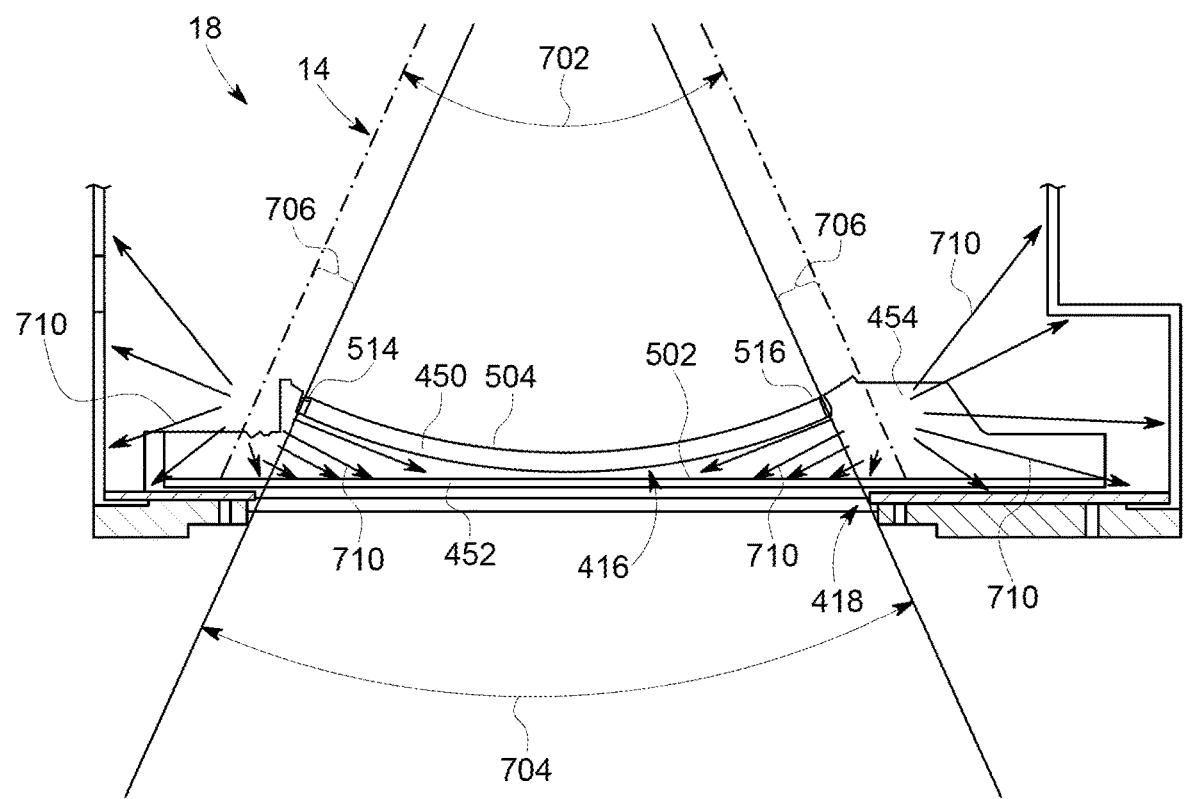
FIG. 8 is a cross-sectional view of the collimator illustrating an X-ray beam directed from an X-ray source to the collimator.
Figure 9:
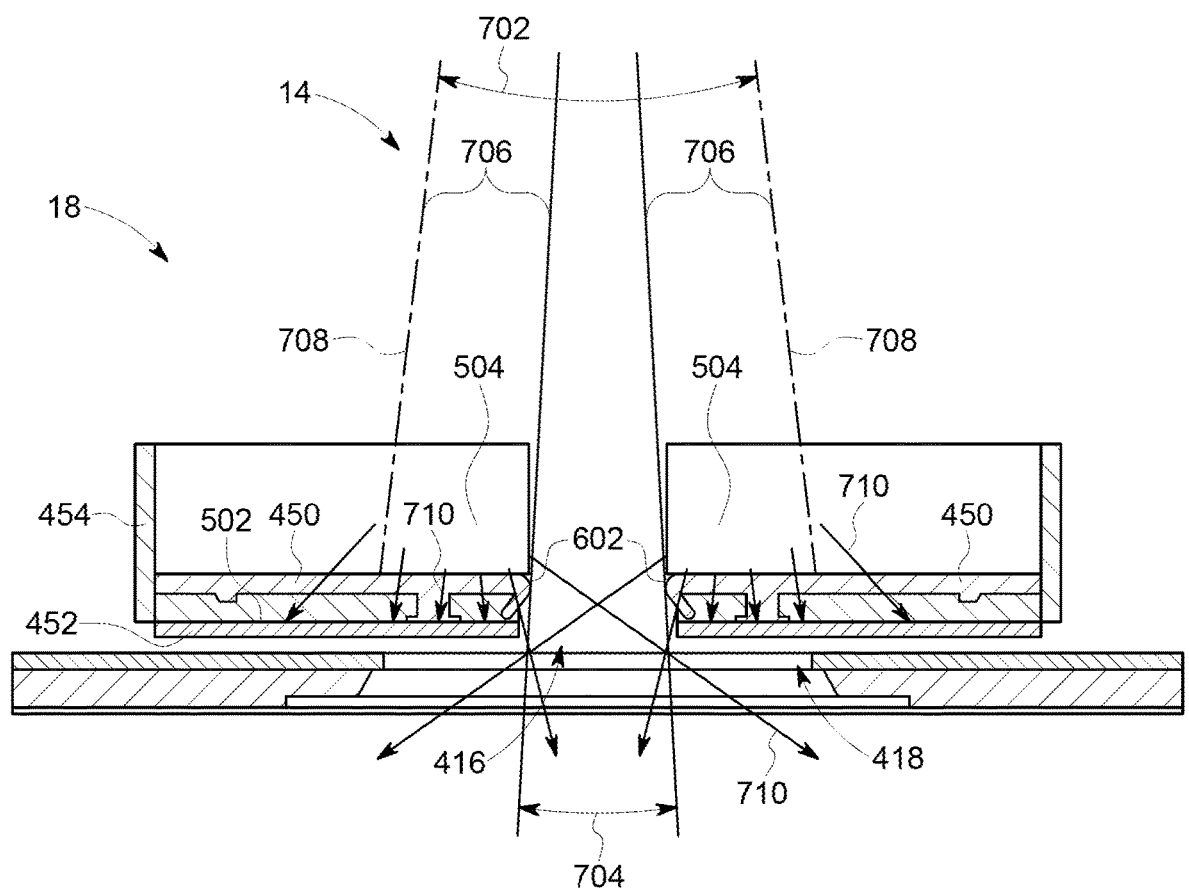
FIG. 9 is another cross-sectional view of the collimator illustrating the X-ray beam directed from the X-ray source to the collimator.

FIG. 8 is a cross-sectional view of the collimator 18 taken along the line 5-5 shown in FIG. 3 illustrating an X-ray beam 14 directed from the X-ray source 12 (shown in FIG. 2) to the collimator 18. FIG. 9 is a cross-sectional view of the collimator 18 taken along the line 6-6 shown in FIG. 3 illustrating the X-ray beam 14 directed from the X-ray source 12 to the collimator 18. The X-ray beam 14 includes an incoming beam 702 that has a beam angle greater than necessary to allow the collimator 18 to shape the X-ray beam 14. The collimator 18 shapes the incoming beam 702 into an outgoing imaging beam 704 that emanates through the aperture 416 and the exit port 418 towards the subject 306 and the detector 20 (both shown in FIG. 2). The imaging beam 704 is utilized for reconstructing images of the subject 306. The outgoing imaging beam 704 has a reduced beam angle relative to the beam angle of the incoming beam 702 because the collimator 18 blocks edge portions 706 of the incoming beam 702 from emanating through the aperture 416 and the exit port 418.

The primary blocking members 450 are responsive for blocking X-rays along the edge portions 706 to trim the X-ray beam 14 for shaping the imaging beam 704. For example, as shown in FIG. 9, the edge portions 706 laterally extend from the inner edges 602 of the primary blocking members 450 to the edges 708 of the incoming beam 702. The X-rays impinge upon the substantially non-planar surfaces 504 and are absorbed or at least attenuated by the primary blocking members 450. As shown in FIG. 9, the outgoing imaging beam 704 is the portion of the incoming beam 702 that laterally aligns between the inner edges 602 of the primary blocking members 450.

The edge portions 706 of the incoming beam 702 that are blocked by the collimator 18 to trim the size and shape of the outgoing imaging beam 704 may result in scatter radiation. For example, as shown in FIG. 8, some of the X-rays along the edge portions 706 may impinge upon the base 454 at or proximate to the ends 514, 516 of the primary blocking member 450, which reflects and refracts scatter X-rays 710 in various directions. The scatter X-rays 710 generally represent rays that have impinged upon another object subsequent to being emitted by the source 12 such that the rays have a lower energy and/or different transmission direction than rays direct from the focal spot of the source 12. Although FIGS. 8 and 9 are two-dimensional illustrations, it is understood that the X-rays 710 scatter in three-dimensions. Some potential sources of scatter within the collimator 18 include the bases 454 (and other non-attenuating portions of the blades), filters, motion control devices (e.g., the rails 442 and actuator 444 shown in FIG. 4), and the like.

The secondary blocking members 452 of the blades 404A, 404B are configured to block scatter radiation from emanating through the exit port 418 towards the subject 306. For example, as shown in FIGS. 8 and 9, at least some of the scatter X-rays 710 impinge upon the substantially planar surfaces 502 of the secondary blocking members 452 and are absorbed. The secondary blocking members 452 may reduce the amount of scatter X-ray radiation that emanates through the collimator 18. As a result, the collimator 18 described herein reduces the amount of lower energy scatter X-ray radiation received by the subject 306 being imaged that does not get detected by the detector 20, and is therefore not utilized for image reconstruction. Relative to known collimators, the collimator 18 may improve the radiation dose efficiency, which is the amount of radiation utilized for image reconstruction (e.g., received by the detector 20) over the amount of radiation applied to the subject 306.

Figure 10:
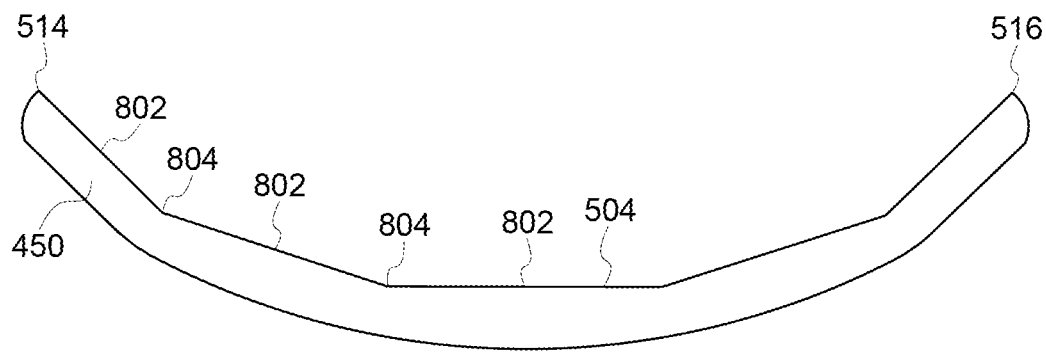
FIG. 10 is a side view of a primary blocking member of one blade of the collimator according to a first alternative embodiment.

FIG. 10 is a side view of the primary blocking member 450 of one of the blades 404 of the collimator 18 according to a first alternative embodiment. The side view of the primary blocking member 450 corresponds to the view shown in FIG. 5. In the illustrated embodiment, the substantially non-planar surface 504 of the primary blocking member 450 has a concave profile that is discontinuous. For example, the surface 504 includes a plurality of segments 802 disposed adjacent to one another between the first and second ends 514, 516 of the primary blocking member 450. Each of the segments 802 has a different angular orientation than an adjacent one of the segments 802. For example, the segments 802 define intersections 804 between adjacent segments 802 due to the different orientations. The segments 802 are linear in FIG. 10, but at least some of the segments 802 may be curved in another embodiment.

Figure 11:
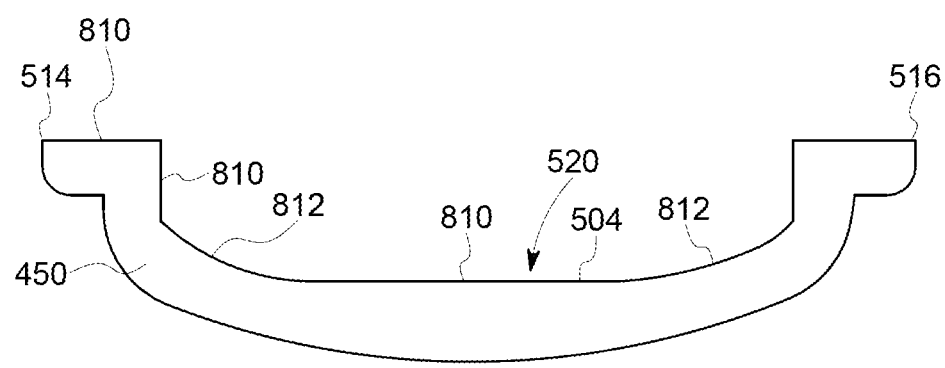
FIG. 11 is a side view of the primary blocking member of the blade of the collimator according to a second alternative embodiment.

FIG. 11 is a side view of the primary blocking member 450 of one of the blades 404 of the collimator 18 according to a second alternative embodiment. The substantially non-planar surface 504 has both linear segments 810 and curved segments 812 along the length between the two ends 514, 516. For example, from the first end 514 towards the second end 516, the surface 504 in FIG. 11 has two linear segments 810 arranged approximately orthogonal to one another, followed by a curved segment 812 and then another linear segment 810 at the middle 520. The surface 504 is symmetrical about the middle 520. In FIG. 11, the surface 504 generally defines a concave profile.

Figure 12:
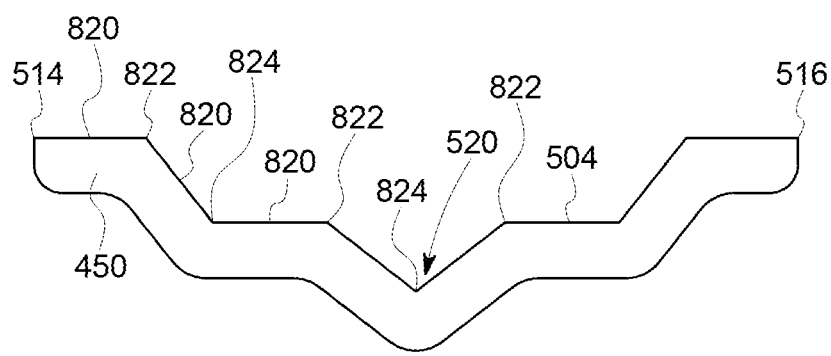
FIG. 12 is a side view of the primary blocking member of the blade of the collimator according to a third alternative embodiment.

FIG. 12 is a side view of the primary blocking member 450 of one of the blades 404 of the collimator 18 according to a third alternative embodiment. In FIG. 12, the substantially non-planar surface 504 has a sawtooth pattern that includes a plurality of segments 820 disposed adjacent to one another along the length between the ends 514, 516. The segments 820 define alternating peaks 822 and valleys 824 at the intersections between adjacent segments 820. The segments 820 are linear in FIG. 12, but at least some of the segments 820 may be curved in another embodiment. The surface 504 is also generally concave in FIG. 11 because the middle 520 is depressed relative to the ends 514, 516.

The shape of the substantially non-planar surface 504 may be designed based on the size and shape of the detector device that detects the X-ray beam through the subject. In other embodiments, the substantially non-planar surface 504 of the primary blocking member 450 may have other shapes than illustrated in FIGS. 5, 10, 11, and 12, such as a V-shape, an undulating shape, or the like. Furthermore, instead of having a concave profile that sinks towards the secondary blocking member 452 (shown in FIG. 5) between the ends 514, 516, the surface 504 may be convex or the like.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. Dimensions, types of materials, orientations of the various components, and the number and positions of the various components described herein are intended to define parameters of certain embodiments, and are by no means limiting and are merely example embodiments. Many other embodiments and modifications within the spirit and scope of the claims will be apparent to those of ordinary skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the invention, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A collimator comprising: a panel defining an exit port through which an X-ray beam from an X-ray source emanates towards a detector; and one or more blades held between the panel and the X-ray source and covering at least a portion of the exit port, each of the one or more blades having a primary blocking member and a secondary blocking member with material densities sufficient to block X-ray radiation, the primary blocking member configured to shape the X-ray beam that is emanated through the exit port, the secondary blocking member secured in a fixed position relative to the primary blocking member between the primary blocking member and the panel to block scatter radiation from the X-ray beam from emanating through the exit port,
wherein the primary blocking member has a substantially non-planar surface facing toward the X-ray source and the secondary blocking member has a substantially planar surface facing toward the X-ray source, and
wherein each of the one or more blades includes a base that engages and holds both the primary blocking member and the secondary blocking member, the base having a material density that is less than the material densities of the primary blocking member and the secondary blocking member.

2. The collimator of claim 1, the base has a first side and a second side opposite the first side, the primary blocking member mounted along the first sine of the base, the respective secondary blocking member mounted along the second side of the base.

3. The collimator of claim 1, wherein the one or more blades includes a first blade and a second blade spaced apart from each other to define an aperture, the aperture having a depth that includes a first passage and a second passage, the first passage defined between respective inner edges of the primary blocking members of the first and second blades, the second passage defined between respective inner edges of the secondary blocking members of the first and second blades, the second passage disposed between the first passage and the exit port.

4. The collimator of claim 1, wherein at least one of the one or more blades is movable relative to the panel to adjust the portion of the exit port covered by the one or more blades for shaping the X-ray beam that is emanated through the exit port.

5. The collimator of claim 1, wherein the substantially non-planar surface of the primary blocking member of each of the one or more blades has a concave profile relative to the secondary blocking member of the respective blade such that a middle of the concave profile is closer to the secondary blocking member than each of a first end and a second end of the concave profile.

6. The collimator of claim 5, wherein the concave profile is a continuous curve extending from the first end of the concave profile to the second end.

7. The collimator of claim 5, wherein the concave profile is discontinuous and includes a plurality of segments disposed adjacent to one another between the first and second ends of the concave profile, each of the segments having a different angular orientation than an adjacent one of the segments.

8. The collimator of claim 1, wherein the substantially non-planar surface of the primary blocking member has a sawtooth pattern that includes a plurality of segments disposed adjacent to one another, the segments defining alternating peaks and valleys along a length of the substantially non-planar surface.

9. The collimator of claim 1, wherein the substantially non-planar surface of the primary blocking member has both linear segments and curved segments along a length of the substantially non-planar surface.

10. The collimator of claim 1, further comprising a housing that defines a cavity, the panel that defines the exit port disposed along a wall of the housing, the panel having a material density sufficient to block X-ray radiation, the one or more blades disposed within the cavity of the housing.

11. The collimator of claim 1, wherein the secondary blocking member is a planar plate that is stacked between the primary blocking member and the panel, and the substantially planar surface of the secondary blocking member is disposed underneath the substantially non-planar surface of the primary blocking member relative to the X-ray source.

12. The collimator of claim 1, wherein the primary blocking member includes one or more of lead, tungsten, or tungsten polymer.

13. A collimator comprising:
a panel defining an exit port configured to allow an X-ray beam from an X-ray source to emanate therethrough towards a detector; and
one or more blades held between the panel and the X-ray source and covering at least a portion of the exit port, each of the one or more blades comprising:
a base having a first side facing the X-ray source;

a primary blocking member mounted to the first side of the base, the primary blocking member having a material density sufficient to block X-ray radiation, the primary blocking member having a substantially non-planar surface facing toward the X-ray source that is configured to shape the X-ray beam that is emanated through the exit port; and a secondary blocking member mounted to the base in a fixed position relative to the primary blocking member and disposed between the primary blocking member and the panel, the secondary blocking member having a material density sufficient to block X-ray radiation, the secondary blocking member including a substantially planar surface facing toward the X-ray source that is configured to block scatter X-ray radiation from emanating through the exit port, wherein the substantially non-planar surface of the primary blocking member has a concave profile relative to the secondary blocking member such that a middle of the concave profile is closer to the secondary blocking member than each of a first end and a second end of the concave profile.

14. The collimator of claim 13, wherein the concave profile is a continuous curve extending from the first end of the concave profile to the second end.

15. The collimator of claim 13, wherein the concave profile is discontinuous and includes a plurality of segments disposed adjacent to one another between the first and second ends of the concave profile, each of the segments having a different angular orientation than an adjacent one of the segments.

16. The collimator of claim 13, wherein the substantially non-planar surface of the primary blocking member has both linear segments and curved segments along a length of the concave profile.

17. The collimator of claim 13, wherein the secondary blocking member is a planar plate that is mounted to a second side of the base that is opposite the first side.

18. The collimator of claim 13, wherein the one or more blades includes a first blade and a second blade spaced apart from each other to define an aperture, the aperture having a depth that includes a first passage and a second passage, the first passage defined between respective inner edges of the primary blocking members of the first and second blades, the second passage defined between respective inner edges of the secondary blocking members of the first and second blades, the second passage disposed between the first passage and the exit port.

19. A collimator comprising:
a first blade and a second blade spaced apart from each other to define an aperture therebetween, the first and second blades configured to receive an X-ray beam from an X-ray source and to shape the X-ray beam via the aperture, at least one of the first and second blades being moveable relative to other blade to adjust a size of the aperture, each of the first and second blades comprising:
a base having a first side facing the X-ray source and a second side opposite the first side;
a primary blocking member mounted to the first side of the base; and
a secondary blocking member mounted to the second side of the base and secured in a fixed position relative to the primary blocking member,
wherein the primary blocking member and the secondary blocking member have material densities sufficient to block X-ray radiation, the primary blocking member having a substantially non-planar surface facing toward the X-ray source that shapes the X-ray beam, the secondary blocking member having a substantially planar surface facing toward the X-ray source that blocks scatter X-ray radiation,
wherein the aperture has a depth that includes a first passage and a second passage, the first passage defined between respective inner edges of the primary blocking members of the first and second blades, the second passage defined between respective inner edges of the secondary blocking members of the first and second blades.

20. The collimator of claim 19, wherein the substantially non-planar surface of the primary blocking member of each of the one or more blades has a concave profile relative to the secondary blocking member of the respective blade such that a middle of the concave profile is closer to the secondary blocking member than each of a first end and a second end of the concave profile, and wherein the secondary blocking member is a planar plate.

* * * * *